(12) United States Patent
Mauger et al.

(10) Patent No.: US 12,712,070 B2
(45) Date of Patent: Aug. 18, 2026

(54) PREDICTIVE MEDICAL DEVICE CONSULTATION

(71) Applicant: Cochlear Limited, Macquarie University (AU)

(72) Inventors: Stefan Jozef Mauger, Macleod (AU); Alexander von Brasch, Cremorne (AU); Stephen Fung, Dundas Valley (AU); John Michael Heasman, North Turramurra (AU)

(73) Assignee: Cochlear Limited, Macquarie University (AU)

( * ) Notice: Subject to any disclaimer, the term of this patent is extended or adjusted under 35 U.S.C. 154(b) by 135 days.

(21) Appl. No.: 18/260,353

(22) PCT Filed: Jan. 3, 2022

(86) PCT No.: PCT/IB2022/050024

§ 371 (c)(1),
(2) Date: Jul. 5, 2023

(87) PCT Pub. No.: WO2022/149056

PCT Pub. Date: Jul. 14, 2022

(65) Prior Publication Data

US 2024/0304314 A1 Sep. 12, 2024

Related U.S. Application Data

(60) Provisional application No. 63/135,844, filed on Jan. 11, 2021.

(51) Int. Cl.
*G16H 40/20* (2018.01)
*A61B 5/00* (2006.01)
(Continued)

(52) U.S. Cl.
CPC ............. *G16H 40/20* (2018.01); *A61B 5/123* (2013.01); *A61B 5/7267* (2013.01); *A61B 5/7275* (2013.01); *G16H 50/20* (2018.01)

(58) Field of Classification Search
CPC ........ G16H 40/20; G16H 50/20; A61B 5/123; A61B 5/7267; A61B 5/7275; A61B 5/121;
(Continued)

(56) References Cited

U.S. PATENT DOCUMENTS 6,496,585 B1 12/2002 Margolis
8,366,632 B2 2/2013 Thornton et al.
(Continued)

FOREIGN PATENT DOCUMENTS

WO 2018006979 A1 1/2018
WO 2018209406 A1 11/2018
WO WO-2022106870 A1 * 5/2022 ............. G06N 20/00

OTHER PUBLICATIONS

Sanderson AP, Rogers ETF, Verschuur CA, Newman TA. Exploiting Routine Clinical Measures to Inform Strategies for Better Hearing Performance in Cochlear Implant Users. Front Neurosci. Jan. 15, 2019;12:1048. doi: 10.3389/fnins.2018.01048. PMID: 30697145; PMCID: PMC6340939. (Year: 2018).*
(Continued)

*Primary Examiner* — Sun M Li
(74) *Attorney, Agent, or Firm* — Edell, Shapiro & Finnan, LLC

(57) ABSTRACT

Presented herein are predictive consultation techniques for use with medical devices. The techniques presented herein, sometimes referred to herein as "predictive medical device consultation techniques," can include, for example, generation of one or more clinical predictions related to timing of future clinical appointments and/or one or more clinical
(Continued)

predictions related to the selection of a medical device for the recipient.

20 Claims, 11 Drawing Sheets

(51) Int. Cl.
*A61B 5/12* (2006.01)
*G16H 50/20* (2018.01)

(58) Field of Classification Search
CPC .......... G06Q 10/0631; G06Q 10/0637; G06Q 10/10; G06Q 50/22
See application file for complete search history.

(56) References Cited

U.S. PATENT DOCUMENTS

| | | | | |
|---|---|---|---|---|
| 8,394,032 | B2 | 3/2013 | Cromwell et al. | |
| 9,339,216 | B2 * | 5/2016 | Fausti | A61B 5/123 |
| 9,480,418 | B2 | 11/2016 | Fausti et al. | |
| 9,560,991 | B2 | 2/2017 | de Vries et al. | |
| 10,078,859 | B2 | 9/2018 | Sable | |
| 10,332,189 | B2 | 6/2019 | Sable | |
| 10,631,113 | B2 | 4/2020 | Mishra et al. | |
| 10,806,405 | B2 * | 10/2020 | Mauger | A61B 5/7275 |
| 2005/0124375 | A1 | 6/2005 | Nowosielski | |
| 2009/0177113 | A1 * | 7/2009 | Cromwell | G16H 15/00 706/46 |
| 2012/0130271 | A1 * | 5/2012 | Margolis | A61B 5/123 600/559 |
| 2013/0023787 | A1 * | 1/2013 | Dowd | G16H 40/20 600/595 |
| 2017/0150282 | A1 | 5/2017 | Mishra et al. | |
| 2017/0300631 | A1 | 10/2017 | Bertrand et al. | |
| 2018/0160984 | A1 * | 6/2018 | Mauger | A61B 5/7275 |
| 2019/0076065 | A1 * | 3/2019 | Lineaweaver | H04R 25/70 |
| 2019/0311419 | A1 | 10/2019 | Sable | |
| 2019/0385744 | A1 * | 12/2019 | Freeman | G16H 80/00 |
| 2020/0204936 | A1 * | 6/2020 | Mathurine | A61B 5/12 |
| 2020/0268260 | A1 * | 8/2020 | Tran | A61B 1/00194 |
| 2021/0092537 | A1 * | 3/2021 | Gozzelino | H04R 25/70 |
| 2021/0106236 | A1 * | 4/2021 | Tran | A61B 5/02055 |
| 2021/0158964 | A1 * | 5/2021 | Yuds | A61B 5/20 |
| 2022/0007116 | A1 * | 1/2022 | Lunner | H04R 25/30 |
| 2023/0338736 | A1 * | 10/2023 | Gibson | A61B 5/746 |
| 2023/0401483 | A1 * | 12/2023 | Chalupper | G06Q 10/04 |

OTHER PUBLICATIONS

Henshaw H, Ferguson MA. Efficacy of individual computer-based auditory training for people with hearing loss: a systematic review of the evidence. PLoS One. May 10, 2013;8(5):e62836. doi: 10.1371/journal.pone.0062836. PMID: 23675431; PMCID: PMC3651281. (Year: 2013).*

Holt RF. Assistive Hearing Technology for Deaf and Hard-of-Hearing Spoken Language Learners. Educ Sci (Basel). Jun. 2019;9(2):153. doi: 10.3390/educsci9020153. Epub Jun. 19, 2019. PMID: 34113551; PMCID: PMC8189502. (Year: 2019).*

Saak SK, Hildebrandt A, Kollmeier B, Buhl M. Predicting Common Audiological Functional Parameters (CAFPAs) as Interpretable Intermediate Representation in a Clinical Decision-Support System for Audiology. Front Digit Health. Dec. 15, 2020;2:596433. doi: 10.3389/fdgth.2020.596433. PMID: 34713064; (Year: 2020).*

J. A. Gahan and B. Kane, "Determining User Requirements for an Audiology Information System," 2018 IEEE 31st International Symposium on Computer-Based Medical Systems (CBMS), Karlstad, Sweden, 2018, pp. 268-273, doi: 10.1109/CBMS.2018.00054. (Year: 2018).*

H. Patel et al., "User Involvement in Design and Application of Virtual Reality Gamification to Facilitate the Use of Hearing Aids," 2016 International Conference on Interactive Technologies and Games (ITAG), Nottingham, UK, 2016, pp. 77-81, doi: 10.1109/iTAG.2016.19. (Year: 2016).*

Convery E, Keidser G, McLelland M, Groth J. A Smartphone App to Facilitate Remote Patient-Provider Communication in Hearing Health Care: Usability and Effect on Hearing Aid Outcomes. Telemed J E Health. Jun. 2020;26(6):798-804. doi: 10.1089/tmj.2019.0109. Epub Aug. 21, 2019. MID: 31433259; PMCID: PMC7301 (Year: 2020).*

M. Gargouri, M. Chaoui and P. Wira, "Development of hearing self-assessment pure tone audiometer," 2020 IEEE International Conference on Design & Test of Integrated Micro & Nano-Systems (DTS), Hammamet, Tunisia, 2020, pp. 1-5, doi: 10.1109/DTS48731.2020.9196165. (Year: 2020).*

International Search Report and Written Opinion in counterpart International Application No. PCT/IB2022/050024, mailed Apr. 12, 2022, 12 pages.

Kurnaz, Dr. Sefer et al., "Predict the type of hearing aid for audiology patients using data mining techniques," IICEMIS '18: Proceedings of the Fourth International Conference on Engineering & MIS 2018, Article No. 57, https://doi.org/10.1145/3234698.3234755, Jun. 19, 2018, 5 pages.

* cited by examiner

220
OBTAIN AUDIOLOGICAL DATA AND INDIVIDUALIZED RECIPIENT DATA
222
GENERATE FIRST FUTURE HEARING OUTCOME ASSOCIATED WITH USE OF A FIRST HEARING DEVICE
224
GENERATE SECOND FUTURE HEARING OUTCOME ASSOCIATED WITH USE OF A SECOND HEARING DEVICE
226
COMPARE FIRST AND SECOND FUTURE HEARING OUTCOMES
228
GENERATE HEARING DEVICE RECOMMENDATION
230

340
dBSL
f
6 MONTHS 340
342
dBSL
f
6 MONTHS 344
340
dBSL
f 440
dB SPL
f
6 MONTHS 442
440
dB SPL
f
6 MONTHS 444
440
dB SPL
f

816
STIMULATING
ASSEMBLY
844(2)
844(3)
844(1)
812
836
834
838
814
852
815
SKIN/TISSUE
802
VESTIBULAR NERVE
STIMULATOR SYSTEM
805
850
808
EXTERNAL
DEVICE
804
890
885
880

PREDICTIVE MEDICAL DEVICE CONSULTATION

BACKGROUND

Field of the Invention

The present invention generally relates to medical devices, such as hearing devices.

Related Art

Medical devices have provided a wide range of therapeutic benefits to recipients over recent decades. Medical devices can include internal or implantable components/devices, external or wearable components/devices, or combinations thereof (e.g., a device having an external device communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: at a computing device: obtaining audiological data representing hearing capabilities of a recipient; obtaining personal data of the recipient; determining an estimated time for a future clinical appointment for the recipient based on an analysis of the audiological data and the personal data; and providing an indication of the estimated time for the future clinical appointment to a user.

In another aspect, a method is provided. The method comprises: at a computing device: obtaining audiological data representing hearing capabilities of a recipient; obtaining personal data of the recipient; generating a recommendation of a hearing device for the recipient based on an analysis of the audiological data and the personal data; and providing an indication of the hearing device to a user.

In another aspect, one or more non-transitory computer readable storage media are provided. The one or more non-transitory computer readable storage media comprise instructions that, when executed by a processor, cause the processor to: obtain sensory data representing sensory deprivation of at least one sense of a recipient of a sensory medical device; obtain personal data of the recipient; predict, based on the sensory data and the recipient data, one or more future outcomes for the recipient, wherein at least one of the one or more future outcomes are associated with future use of at least one medical sensory device by the recipient to treat the sensory deprivation; generate, based on the one or more future outcomes for the recipient, at least one recommendation of a first sensory device for the recipient; and provide an indication of the first sensory medical device to a user of the computing device.

In another aspect, a computing device is provided. The computing device comprises: one or more network interface units; memory; a display screen; and one or more processors configured to: analyze data associated with a recipient of a sensory prosthesis to determine an estimated time for a future clinical appointment for the recipient; and display an indication of the estimated time for the future clinical appointment to a user via the display screen.

In another aspect, a computing device is provided. The computing device comprises: one or more network interface units; memory; a display screen; and one or more processors configured to: analyze data associated with a recipient of a sensory prosthesis to generate a recommendation of a sensory device for the recipient; and display an indication of the recommendation to a user via the display screen.

BRIEF DESCRIPTION OF THE DRAWINGS

Embodiments of the present invention are described herein in conjunction with the accompanying drawings, in which.

DETAILED DESCRIPTION

Figure 1:
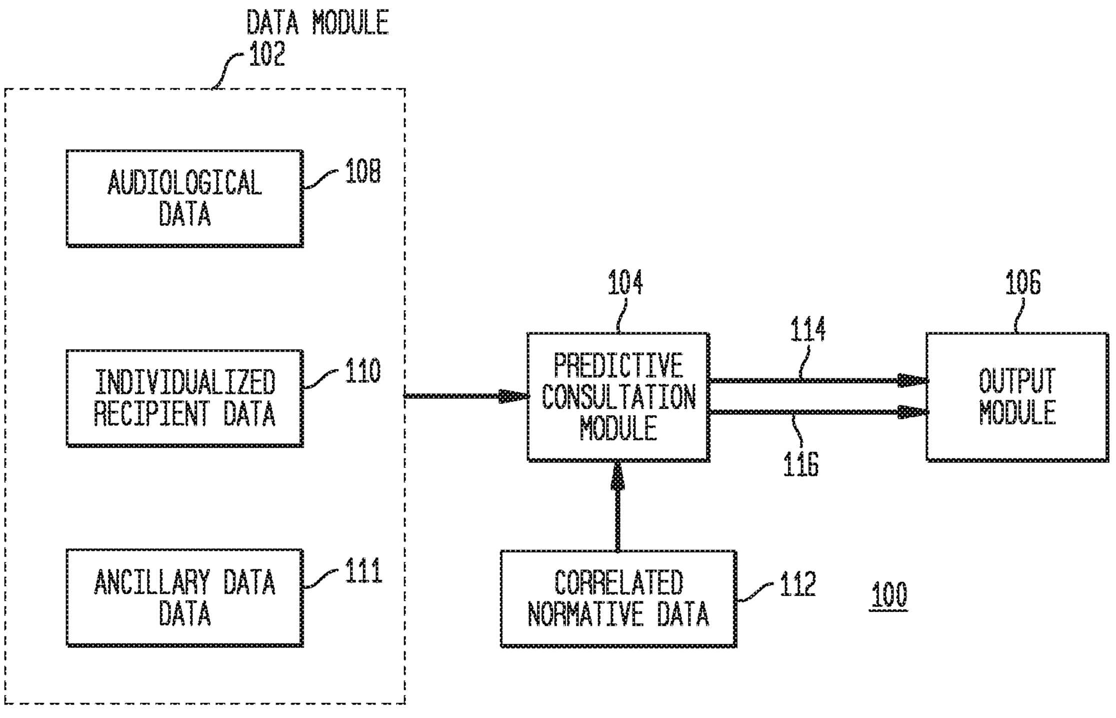
FIG. 1 is a schematic diagram of a predictive medical device consultation system, in accordance with certain embodiments presented herein.

Presented herein are predictive consultation techniques for use with medical devices. The techniques presented herein, sometimes referred to herein as "predictive medical device consultation techniques," can include, for example, generation of one or more clinical predictions related to timing of future clinical appointments and/or one or more clinical predictions related to the selection of a medical device for the recipient.

Merely for ease of description, the predictive medical device consultation techniques presented herein are primarily described with reference to sensory medical devices (sensory devices) and, more specifically, hearing devices. However, it is to be appreciated that the techniques presented herein may also be implemented in associated with other types of medical devices. For example, the techniques presented herein may be implemented with a variety of hearing devices, such as hearing aids, middle ear auditory prostheses, bone conduction devices, direct acoustic stimulators, electro-acoustic prostheses, auditory brain stimulators, etc. The techniques presented herein may also be used with other types of medical devices, including other types of sensory devices, such as vestibular devices (e.g., vestibular implants), visual devices (e.g., bionic eyes), etc., tinnitus therapy devices, sensors, pacemakers, drug delivery systems, defibrillators, functional electrical stimulation devices, catheters, seizure devices (e.g., devices for monitoring and/or treating epileptic events), sleep apnea devices, electroporation devices, etc.

As used herein, a "recipient" of a hearing device or other medical device is a person who has been prescribed with a medical device (e.g., a person that currently uses a particular medical device), or a person who is a candidate to be prescribed with a medical device (e.g., a person who may use a medical device in the future) now or in the future. For example, hearing device recipients may include individuals who suffer from some sensory loss (e.g., hearing loss, balance loss, vision loss, etc.) or individuals who do not yet suffer any sensory loss.

As noted above, merely for ease of description, the techniques presented herein are primarily described with reference to hearing devices and hearing device recipients. The rehabilitation journey of a hearing device recipient, in particular, typically begins with some form of audiological testing to determine whether the recipient suffers from hearing loss and/or to determine the type of hearing loss, degree of hearing loss, etc. If hearing loss is present, a clinician, audiologist, or other medical practitioner uses the results of the testing, as well as her clinical experience, to prescribe the recipient with a hearing device.

Clinical prescription of a correct type of hearing device (e.g., hearing aid, high-power hearing aid, bone conduction device, cochlear implant, etc.) to a recipient is of critical importance. The prescription of an inappropriate hearing device may directly impair the recipient's ability to safely and effectively perform their daily routine/interactions, as well as impair their hearing rehabilitation. The clinical prescription process generally requires the medical practitioner to assess the recipient's hearing needs, based on the recipient's audiological testing (e.g., audiogram) and the medical practitioner's clinical experience.

As a recipient's hearing journey continues, the recipient may return to a clinic at regular intervals or in an ad hoc manner when, for example, the recipient experiences a problem with his/her hearing device. Depending on the recipient's living situation, location, insurance, clinic shortages, etc., it may be difficult for some recipients to gain access to an audiologist/clinician. However, missing the optimal time to being using a hearing device, change the recipient's hearing device settings, switch to a more suitable type of hearing device, etc. could potentially put the recipient at risk of achieving sub-optimal outcomes for his/her hearing perception and/or speech development. Currently, recipients must solely depend on these clinical visits and consultation from the audiologist/clinician to understand his/her own hearing perception changes (i.e., audiogram) for hearing device selection.

As noted, one of the challenges associated with hearing devices, and cochlear implants in particular, is to determine the optimal time to implant the cochlear implant in a recipient. If a recipient waits too long to undergo the cochlear implantation, then her hearing may degrade significantly, and her brain and auditory system can begin to 'switch-off.' In such cases, the recipient may be unable to recover and rehabilitate with the cochlear implant, thereby achieving poor hearing outcomes.

Presented herein are techniques that provide personalized and optimized healthcare consultation services for recipients of hearing devices and other medical devices, including other sensory devices. With reference to hearing devices, the techniques presented herein enable recipients to undergo changes to their hearing device at the optimal time, as well as to gain clinical access at optimal times, so as to achieve the best possible hearing outcomes.

More specifically, and as described further below, the techniques presented herein analyze a recipient's audiological data (e.g., audiograms measured at various times) and predict, based on the audiological data, in combination with other factors/measures, how the recipient's hearing is likely to evolve over time with or without the assistance of one or more hearing devices. As described further below, the other factors/measures can include personal data associated with the recipient, as well as ancillary data, such as hearing or medical device attributes (e.g., device size, device aesthetics, device battery use information, device wearing method, etc.), costs associated with a particular device, clinical time associated with use of a medical device, etc.

As such, the techniques presented can then determine an optimal (in terms of best possible hearing outcomes) a particular hearing device for a recipient, determine an optimal time for a recipient to be prescribed a particular hearing device, determine the optimal time to change between hearing devices, etc. Also as described below, the techniques presented herein can also analyze a recipient's audiological data and predict, based on the audiological data, in combination with other factors/measures, an estimated timing for one or more future clinical appointments.

FIG. 1 is a schematic diagram illustrating functional aspects of a predictive medical device consultation system 100, in accordance with certain embodiments presented herein. Merely for ease of illustration, the predictive medical device consultation system 100 of FIG. 1 will generally be described with reference to hearing devices and hearing device recipients. However, as noted above, the techniques presented herein can be used with other types of medical devices and, as such, the example of FIG. 1 is merely illustrative.

As shown, the predictive medical device consultation system 100 generally comprises a data module 102, a predictive consultation module 104, and an output module 106. It is to be appreciated that the modules 102, 104, and 106 illustrate functional aspects of the techniques presented herein and do not necessarily correspond to any specific structural arrangement. As such, each of the modules 102, 104, and 106 can be implemented across the same or different one or more physical or virtual computing devices and at one or more of the same or different locations.

The data module 102 generally comprises/includes information/data for analysis by the predictive consultation module 104. In one example implementation, the data module 102 may be embodied as one or more databases hosted on one or more physical or virtual servers (e.g., a data store).

In the example of FIG. 1, the data module 102 includes audiological data 108 and individualized recipient data 110. The audiological data 108 comprises data representing the unaided (e.g., without the assistance of a hearing device) and/or aided (e.g., with the assistance of a hearing device) hearing ability of a recipient, potentially over a period time. For example, the audiological data 108 can comprise a recipient's audiogram measured at various points in times (e.g., plotted results of pure tone audiometry hearing tests conducted over the course of days, weeks, months, or years) and/or data representing changes in audiograms over time. The audiological data 108 can also or alternatively include other measures of the recipient's hearing abilities, such as speech test results/scores (e.g., Speech Reception Threshold (SRT) results, Words in Quiet Scores, Word Recognition Scores, Threshold Tests, Digit Triple Tests, etc.), bone conduction test data, tympanometry data, Acoustic Reflex Testing data, static acoustic impedance data, Auditory Brainstem Response (ABR) data, Otoacoustic Emission (OAE) data, device usage log data over time (e.g., indicating auditory DIET, changes made, recorded alarms or issues experienced etc.), psychophysics measures, such as impedances, neural response telemetry (NRT) data, Electrical Evoked Stapedial Reflex Thresholds (eSRTs), Electrocochleography (ECOG) data, etc.

The individualized recipient data 110 can comprise, for example, personal attributes/data associated with a specific recipient. For example, the individualized recipient data 110 can include the age, medical condition(s), language, location(s), current device settings, typical sound environments, preferences, etc. of the specific recipient. The recipient data 110 can also include other factors, such as the specific recipient's psychoacoustic characteristics, family genetic history, personal medical background, etc. Separate individualized recipient data 110 is generated for each recipient receiving the predictive medical device consultation described herein.

It is to be appreciated that the specific illustration of the audiological data 108 and the individualized recipient data 110 is merely illustrative and that, in certain embodiments, additional and/or different types of information may be included as part of the data module 102. For example, in the context of a visual prosthesis, the audiological data 108 could be replaced with visual data (e.g., results of a recipient's vision test(s)), while in the context of a balance prosthesis the audiological data 108 could be replaced with balance data (e.g., results of a recipient's balance test(s)). In general, the content of the data module 102 can be configured for the specific type medical device with which the specific predictive consultation techniques are provided.

Additionally, the additional and/or different types of information can include ancillary data 111. This ancillary data 111 can comprise, for example, hearing or medical device attributes, including device size, device aesthetics, device battery use information, device wearing method (e.g., behind-the-ear, off-the-ear, in-the-ear, etc.), costs associated with a particular device, clinical time associated with use of a medical device, etc. As such, in some forms, the predicted "future outcomes" include not only device performance and/or treatment metrics related to treatment of a sensory deprivation (e.g., how much hearing benefit is provided), but also "outcomes" in terms of costs/expenses, clinical time, recipient preferences, etc.

Returning to the example of FIG. 1, the predictive consultation module 104 is, or includes, a machine learning model or other type of Artificial Intelligence (AI) system, such as an Artificial Neural Network (ANN), that is configured to analyze the audiological data 108 and the individualized recipient data 110, and in certain cases the ancillary data 111, to generate one or more clinical predictions 114. The one or more clinical predictions may be, for example, related to timing of future clinical appointments and/or to the selection of a medical device for the recipient.

The AI system (e.g., predictive consultation module 104) is trained to generate the one or more clinical predictions 114 based on correlated normative data 112. In general, the correlated normative data 112 is historical data obtained from a large population of different hearing device recipients, which has been analyzed and associated together in a meaningful way based on one or more factors or metrics. The correlated normative data 112 may comprise, for example, different types of audiological data or ancillary data that is correlated based on different types of individualized recipient data (e.g., audiograms correlated by hearing loss type and age). The correlated normative data 112 can be embodied as a pre-built database or that is updated periodically/dynamically (e.g., in real-time) in response to recipient fittings, testing, etc., and be used to periodically/dynamically re-train or update the AI system. Although shown as a separate element, the correlated normative data 112 may, for example, be part of the data module 102, predictive consultation module 104, etc.

In one example implementation, the predictive consultation module 104 is configured to analyze (as trained using the correlated normative data 112) the recipient's audiological data 108 (e.g., audiograms, hearing perception data, etc.) and individualized recipient data 110 to predict the recipient's future hearing outcomes 114 (e.g., hearing outcomes at some point in the future, in six months, one year, two years, etc.) with the aid of different hearing devices and/or unaided hearing outcomes. That is, in these examples, the one or more clinical predictions 114 comprise future hearing outcome predictions representing how the recipient's hearing is likely to evolve over the course of a future period with the aid of various hearing devices and/or without the aid of hearing devices. In one embodiment, a clinical prediction 114 may be generated as a "forecast audiogram," where the forecast audiogram is an estimation of the recipient's audiogram in the future (e.g., in six months, one year, two years, etc.) if he/she uses each of a number of different hearing devices and/or does not use any hearing device. The use of a forecast audiogram is merely illustrative and that other representations of future hearing outcomes (e.g., SRT scores) could be used in alternative embodiments.

In accordance with certain embodiments presented herein, the clinical predictions 114 can be provided to a user (e.g., recipient, clinician, etc.) via the output module 106. However, in certain embodiments, the clinical predictions 114 can be further used by the predictive consultation module 104 to generate one or more clinical recommendations 116 for the recipient. The clinical recommendations 116 may comprise, for example, one or more recommendations for the timing of future clinical appointments, one or more recommendations to the selection of a medical device for the recipient, etc. For example, in certain embodiments, using the one or more clinical predictions 114, the predictive consultation module 104 can recommend the optimal point when to change the recipient's hearing device (e.g., begin use of a hearing aid, change from a hearing aid to a high-power hearing aid, change from a hearing aid to bone conduction device, change from a hearing aid to a cochlear implant, acoustic implant, or bone conduction implant, etc.). In addition, using the one or more predictions 114, the predictive consultation module 104 can generate recommendation for the optimal best time to change coding strategies, signal processing algorithms, so to be able to maximize hearing outcomes (for example, to achieve better audiograms).

Furthermore, using the one or more predictions 114, the predictive consultation module 104 can generate a recommendation for the optimal time for the recipient to return to the clinic for a subsequent appointment. That is, the one or more predictions 114 can be used to determine the optimal cadence of appointments for the recipient, with the need (as above) or without the need to change the hearing device. For example, in one embodiment, the predictive consultation module 104 could predict the time period until a certain hearing level change is likely to occur and/or when an audiologist/medical visit is warranted. This time period would likely be longer for recipients with more stable hearing, and shorter for recipients with fluctuating or precipitous hearing loss.

For ease of reference, FIG. 1 has been described with the one or more clinical predictions 114 and one or more clinical recommendations 116 as separate decisions or processes. It is to be appreciated that these decisions/processes can be integrated in various manners to generate the clinical recommendations 116 relating to the timing of future clinical appointments, selection of a medical device for the recipient, etc. That is, the techniques presented herein do not necessarily require the generation of the one or more clinical predictions 114 and one or more clinical recommendations 116 in a serial manner to provide an output to a recipient.

As shown in FIG. 1, the one or more clinical predictions 114 and/or one or more clinical recommendations 116 can be provided to a user (e.g., recipient, caregiver, medical practitioner, etc.) via the output module 106. The output module 106 may be embodied as, for example, a computing device (e.g., laptop computer, tablet computer, fitting system, mobile phone, etc.) with one or more output devices, such as a display screen, speaker, etc.

Conventionally, clinicians deliver care to recipients with an emphasis on a current diagnosis, which is then treated with a prescription. For future care needs of a given recipient, the clinician usually suggests scheduling a "check-up" appointment at a nominal future date, e.g., in six months, at which time there will be a re-assessment and a new prescription if there have been sufficient changes in the diagnosis. For hearing or other medical devices, a new prescription can mean purchasing a replacement device at considerable expense. As such, certain recipient's may request an "over-prescribed" device, in the hope that if his/her hearing or condition deteriorates, then they can save money by not having to immediately pay for a replacement device. However, this practice is rarely reimbursable and usually discouraged as being a potential waste of resources.

The predictive consultation techniques presented herein provide an AI system (e.g., machine learning model), with an associated training method, that provides reliable outputs that are actionable in ways that have not previously been possible. As noted above, the outputs of the model can include predictions of future hearing outcomes with the one or more hearing devices or with unaided hearing, recommendations on which hearing device to use, recommendations on when to transition to a given device, recommendations for future clinical appointment timing, etc. In certain examples, these outputs can, for example, provide personalized device choices that permit the recipient to plan ahead by choosing to have an over-prescribed device (or not) and/or taking into account other factors that are personal to their situation. Moreover, the accuracy and reliability of the machine learning model can provide a direct mechanism for reimbursement and/or more efficient planning for clinical practice management, that had not previously been possible with standard clinical judgement.

Figure 2:
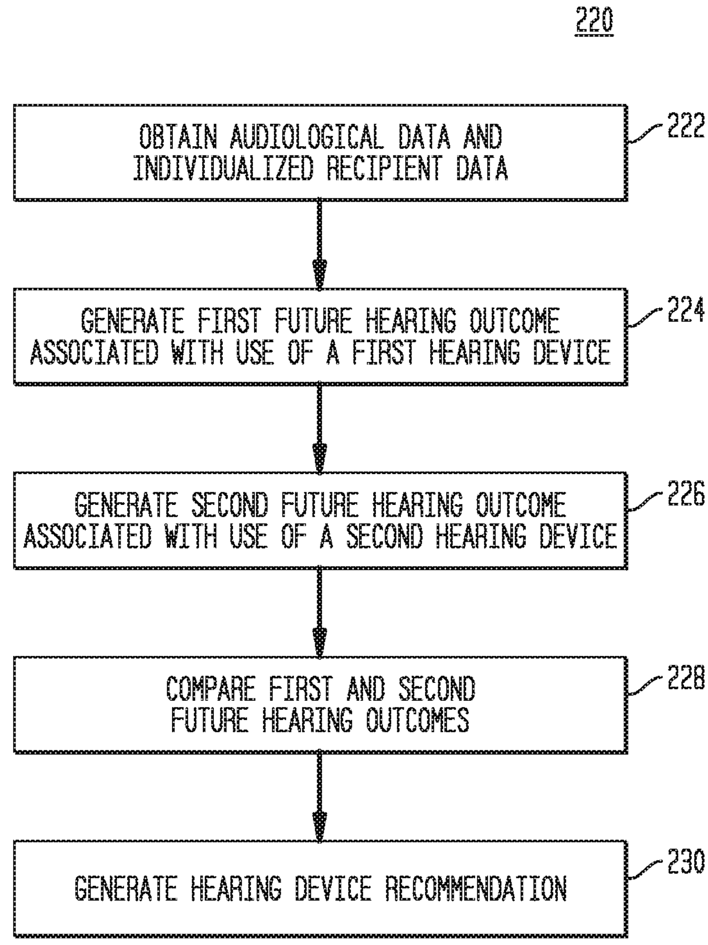
FIG. 2 is a flowchart of an example method, in accordance with certain embodiments presented herein.
Figures 3A, 3B, 3C:
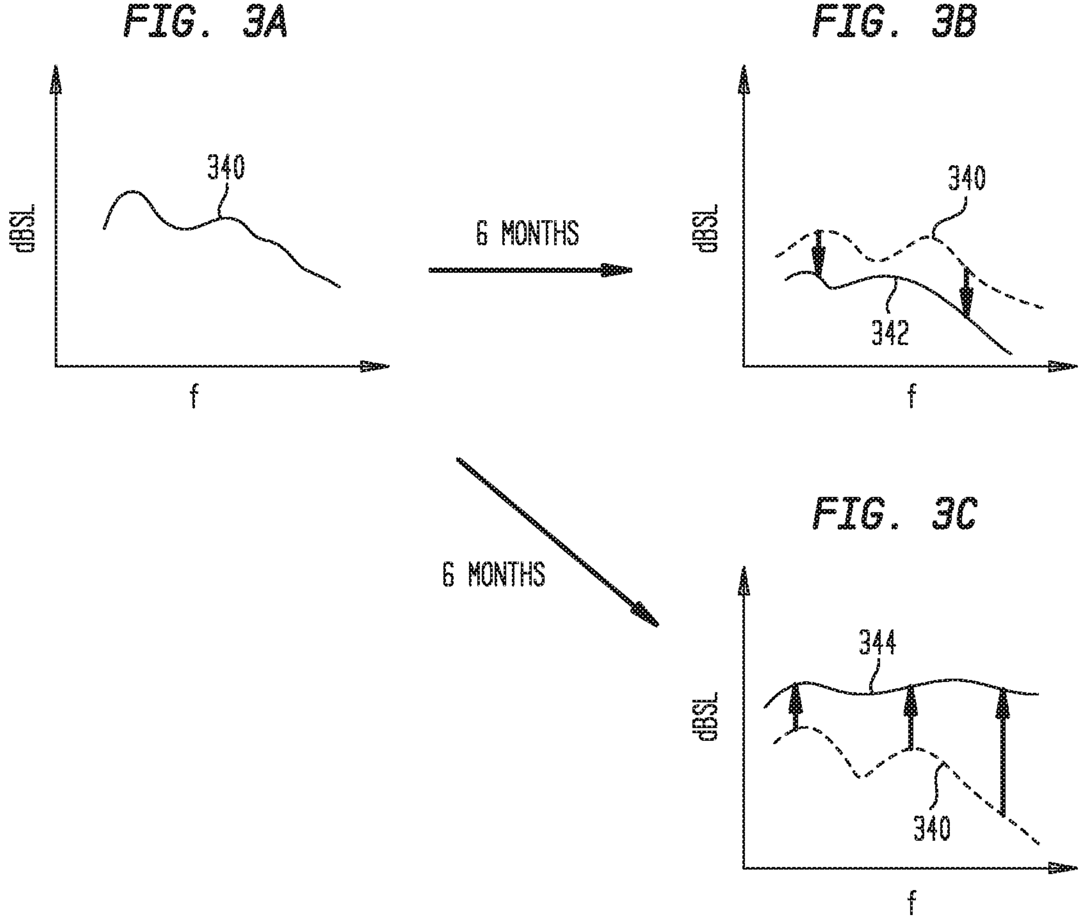
FIG. 3A is a diagram illustrating a current audiogram of a hearing device recipient, in accordance with certain embodiments presented herein.
FIG. 3B is a diagram illustrating a first future hearing outcome associated with the hearing device recipient of FIG. 3A, in accordance with certain embodiments presented herein.
FIG. 3C is a diagram illustrating a second future hearing outcome associated with the hearing device recipient of FIG. 3A, in accordance with certain embodiments presented herein.

FIG. 2 is a flowchart of a method 220, in accordance with embodiments presented herein. For ease of description, the example of FIG. 2 will be described with reference to FIGS. 3A-3C, which are schematic diagrams illustrating current and predicted hearing outcomes associated with a recipient of a hearing device. More specifically, FIG. 3A illustrates a current audiogram 340 of a hearing aid recipient, while using the hearing aid (e.g., FIG. 3A represents the current hearing capabilities of the recipient while using the hearing aid, plotted as Decibels Sensation Level (dB SL) versus frequency (f)). As described below, FIGS. 3B and 3C each represent corresponding a prediction of the recipient's future hearing outcomes, with different hearing devices.

Method 220 begins at 222 where a predictive medical device consultation system, such as system 100 of FIG. 1, obtains or access audiological data and individualized recipient data associated with the hearing aid recipient. As noted, predictive medical device consultation system includes an AI system (predictive consultation module 104) that has been trained, and which can be regularly re-trained or updated, using correlated normative data. At 224, the predictive consultation module 104 generates a first future hearing outcome associated with use of a first hearing device by the recipient. That is in the example of FIG. 2, at 224, the system generates a prediction of the recipient's future hearing capabilities, six (6) months in the future, if the recipient continues to use her hearing aid for those 6 months. The prediction is generated by the AI system based on the audiological data and the individualized recipient data, in view of the correlated normative data training.

As shown in FIG. 3B, the first future hearing outcome is in the form of a forecast audiogram 342 and is shown relative to current audiogram 340. In this example, the first future hearing outcome 342 indicates a degradation/decrease in the hearing outcomes of the recipient through continued use of the hearing aid.

Returning to FIG. 2, at 226, the predictive consultation module 104 generates a second future hearing outcome associated with use of a second hearing device by the recipient. That is, in the example of FIG. 2, at 226, the system generates a prediction of the recipient's future hearing capabilities, six (6) months in the future, if the recipient would be implanted with, and then use, a cochlear implant for those 6 months. Again, the prediction is generated by the AI system based on the audiological data, the individualized recipient data, in view of the correlated normative data training.

As shown in FIG. 3C, the second future hearing outcome is in the form of a forecast audiogram 344 and is shown relative to current audiogram 340. In this example, the second future hearing outcome 344 indicates an improvement/increase in the hearing outcomes of the recipient through use of the cochlear implant.

Returning to FIG. 2, at 228, the system compares the first future hearing outcome and the second future hearing outcome and, based on the comparison, generates a hearing device recommendation at 230. In the examples of FIGS. 2 and 3A-3C, use of the cochlear implant is predicted to lead to an improvement in the recipient's hearing outcomes, while continued increase of the hearing aid is predicted to lead to a degradation in the recipient's hearing outcomes. As such, the predictive consultation module 104 may recommend the recipient receive a cochlear implant.

It is to be appreciated that the examples of FIGS. 2 and 3A-3C are merely illustrative and that the techniques presented herein can be implemented in a number of different manners. For example, in alternative embodiments, the predictive medical device consultation system can generate more than two hearing outcome predictions for analysis relative to one another (e.g., predict hearing outcomes with all of a hearing aid, high power hearing aid, bone conduction device, and cochlear implant for relative analysis).

Figures 4A, 4B, 4C:
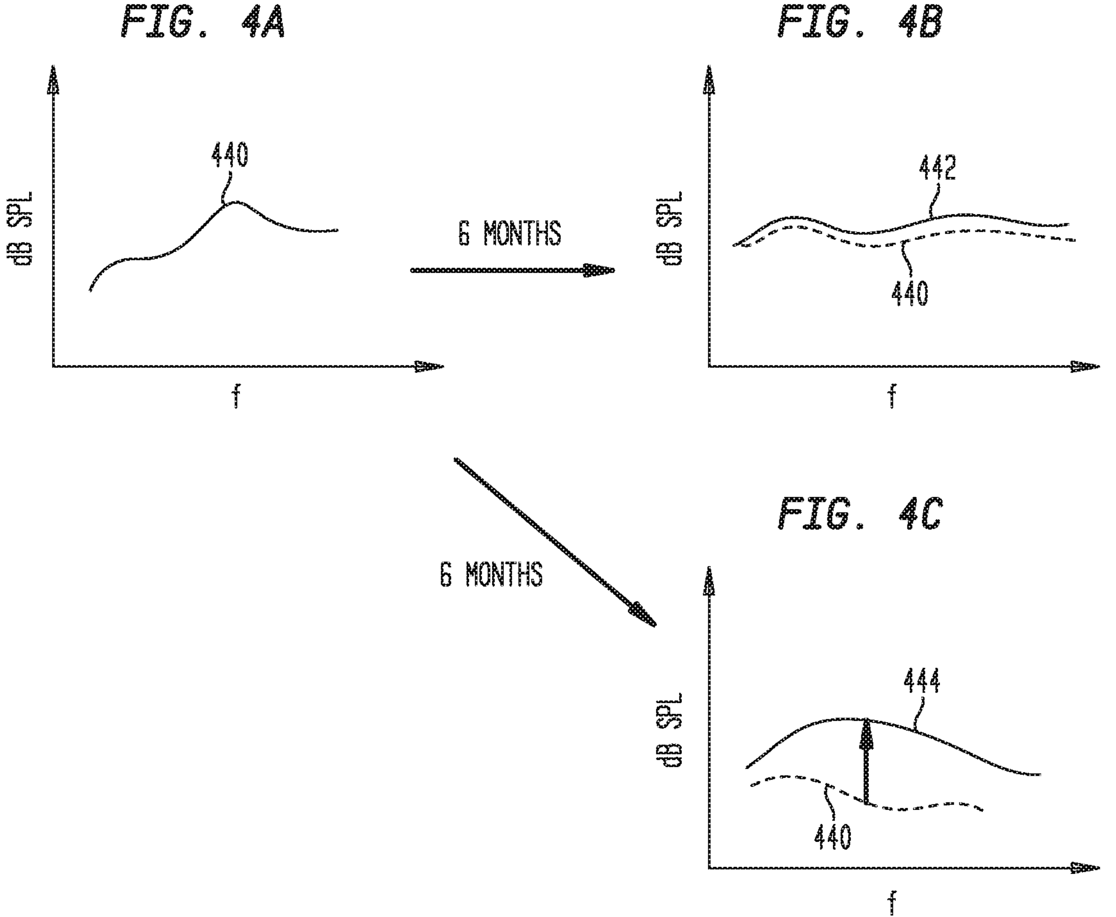
FIG. 4A is a diagram illustrating a current audiogram of a hearing device recipient, in accordance with certain embodiments presented herein.
FIG. 4B is a diagram illustrating a first future hearing outcome associated with the hearing device recipient of FIG. 4A, in accordance with certain embodiments presented herein.
FIG. 4C is a diagram illustrating a second future hearing outcome associated with the hearing device recipient of FIG. 4A, in accordance with certain embodiments presented herein.

The techniques presented herein may also or alternatively account for different device settings when predicting future outcomes. For example, the predictive medical device consultation system could predict future outcomes with a hearing aid using a first group of settings, predict future outcomes with a hearing aid using a second group of settings, predict future outcomes with a cochlear using a first group of settings, predict future outcomes with a cochlear using a second group of settings, and so on, which can then be analyzed relative to one another to recommend a hearing device for the recipient. FIGS. 4A, 4B, and 4C illustrate predictions of future outcomes that account for device settings.

More specifically, FIG. 4A illustrates a current audiogram 440 of a cochlear implant recipient, while using the cochlear (e.g., represents the current hearing capabilities of the recipient while using the cochlear, plotted as Decibels Sound Pressure Level (dB SPL) versus frequency (f)). As described below, FIGS. 4B and 4C each represent the a prediction of the recipient's future hearing outcomes, with different settings for the cochlear implant.

More specifically, as shown in FIG. 4B, the predictive medical device consultation system (e.g., predictive consultation module 104) generates a prediction of the recipient's future hearing capabilities, six (6) months in the future, if the recipient continues to use her cochlear implant with a first group of settings (e.g., the current settings) for those 6 months. In the example of FIG. 4B, the prediction is generated based on the audiological data, the individualized recipient data, and the correlated normative data and is in the form of a forecast audiogram 442, which is shown relative to the current audiogram 440. In this example, the first future hearing outcome 442 indicates an increase in the hearing outcomes of the recipient through continued use of the first group of settings.

As shown in FIG. 4C, the predictive medical device consultation system generates a prediction of the recipient's future hearing capabilities, six (6) months in the future, if the recipient continues to use her cochlear implant with a second group of settings (e.g., different from the current settings) for those 6 months. In the example of FIG. 4C, the prediction is generated based on the audiological data, the individualized recipient data, and the correlated normative data and is in the form of a forecast audiogram 444, which shown relative to the current audiogram 440. In this example, the second future hearing outcome 444 indicates an increase in the hearing outcomes of the recipient through use of the second group of settings.

As shown in FIGS. 4B and 4C, the increase in hearing outcomes associated with the second group of settings exceeds the increase in hearing outcomes associated with the first group of settings. As such, the predictive medical device consultation system may recommend use of the second group of settings with/by the cochlear implant.

Again, it is to be appreciated that the examples of FIGS. 4A-4C are merely illustrative and that the techniques presented herein can be implemented in a number of different manners. For example, in alternative embodiments, the predictive medical device consultation system can generate more than two hearing outcome predictions for analysis relative to one another (e.g., predict hearing outcomes with a larger number of different groups of settings to find the optimal settings for the recipient, based on predicted outcomes).

Figure 5:
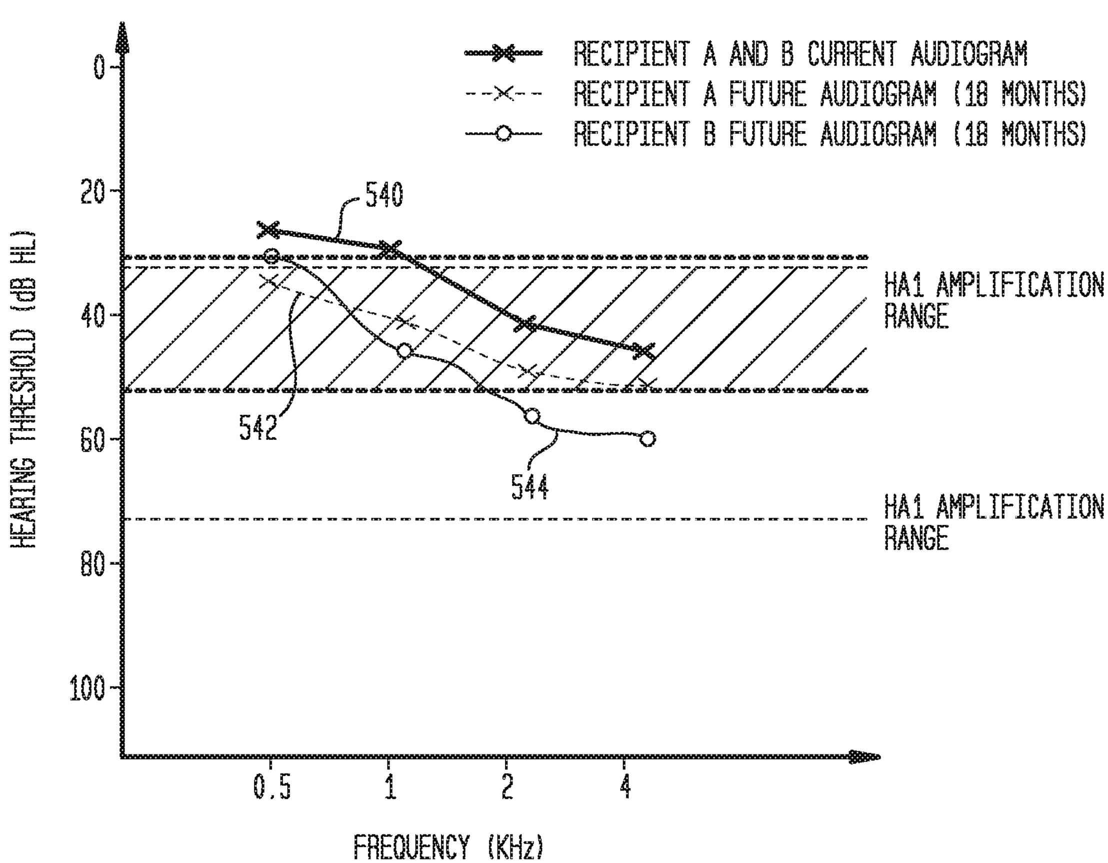
FIG. 5 is a diagram illustrating a current audiogram of first and second hearing device recipients, as well as predicted future hearing outcomes for each of the first and second hearing device recipients, in accordance with certain embodiments presented herein.

FIG. 5 is a diagram illustrating application of the techniques presented herein for different recipients. In particular, illustrates a current audiogram 540 (Decibels Hearing Level (dBHL) versus frequency) associated with two different hearing aid recipients, referred to as Recipient A and Recipient B. In this example, merely for purposes of illustration, it assumed that both recipients begin with the same audiogram.

FIG. 5 further illustrates a first prediction, in the form of a forecast audiogram 542, of the future hearing capabilities of recipient A, eighteen (18) months in the future, if the recipient continues to use her hearing aid for those 18 months. Additionally, FIG. 5 illustrates a second prediction, in the form of a forecast audiogram 544, of the future hearing capabilities of recipient B, eighteen (18) months in the future, if the recipient continues to use her hearing aid for those 18 months. In the example of FIG. 5, the two predictions are generated by an AI system using audiological data and the individualized recipient data for each of the recipients, where the AI system is trained based on correlated normative data.

The forecast audiograms 542 and 544 indicate that, even though both recipients began with the same hearing capabilities, the system predicts that each will experience different hearing outcomes over the course of 18 months. As a result, recipient A may be recommended a hearing aid with less power, while recipient B may be recommended a hearing aid with more power (to compensate for a predicted degradation in hearing capabilities).

Figure 6:
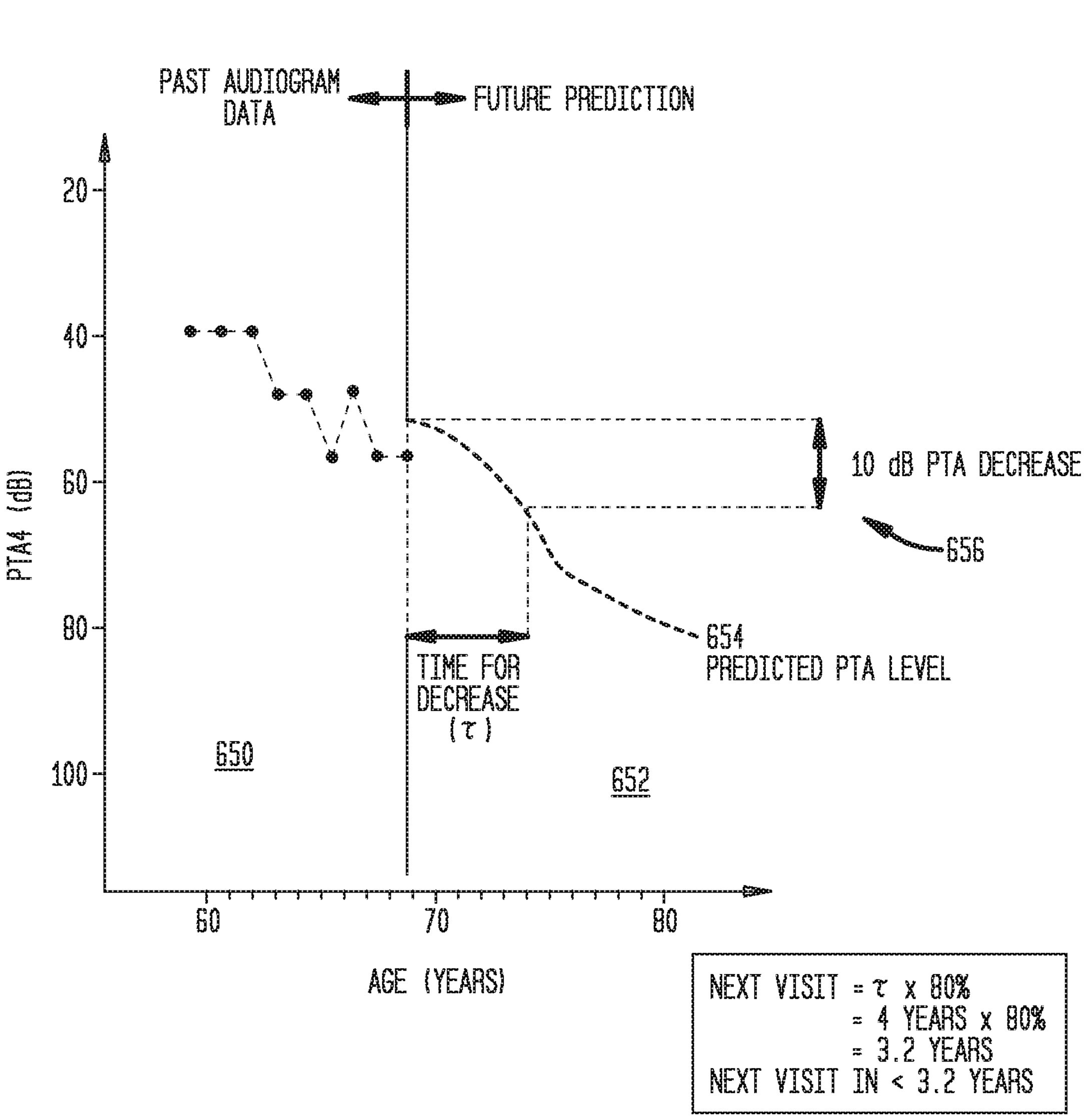
FIG. 6 is a diagram illustrating prediction of a timing for a future clinical appointment for a hearing device recipient, in accordance with certain embodiments presented herein.

FIGS. 2, 3A-3C, 4A-4C, and 5 generally illustrate predictions of how the recipient's hearing is likely to evolve over time with or without the assistance of one or more hearing devices and use of those predictions to recommend particular hearing devices and/or hearing device settings. However, as noted above, the predictions of how the recipient's hearing is likely to evolve over time may also or alternatively be used determine the optimal time (in terms of hearing outcomes) for a recipient to be prescribed a hearing device and/or to determine an estimated timing for one or more future clinical appointments. All of the predictions shown in 3A-3C, 4A-4C, and 5 could alternatively be used for these purposes. FIG. 6 is a diagram illustrating one specific technique for determining an estimated timing for one or more future clinical appointments.

More specifically, FIG. 6 is a graph illustrating a recipient's average hearing threshold (e.g., multiple frequencies), in Decibels (dB), versus the recipient's age. In FIG. 6, the threshold is represented by a Pure Tone Average (PTA), which refers to the average of the hearing threshold levels at a set of specified frequencies. For example, the specific four-frequency PTA4 of FIG. 6 uses 4 tones (e.g., 500 Hz, 1 kHz, 2 kHz, and 4 kHz) to assess the recipient's average hearing (a cross-sectional analysis). Other embodiments could use, for example, PTA3, PTA5, etc. For the case of PTA4, it calculates the mean hearing threshold for 500 Hz, 1 kHz, 2 kHz, and 4 kHz although many more frequencies are frequently available in the audiogram.

In the example of FIG. 6, the recipient in this example is 69 years old and the graph has a first section/portion 650 representing the recipient's historical/past hearing thresholds over time determined, for example, from the recipient's historical audiograms. The graph further includes a second section/portion 652 representing the recipient's predicted hearing thresholds 654 determined by an AI system using the recipient's audiological data and individualized recipient data, where the AI system is trained based using the correlated normative data.

Shown in FIG. 6 is a level 656 associated with a 10 dB decrease in the recipient's predicted hearing threshold level 654. In this example, the predictive medical device consultation system determines the time period (T) until the recipient's hearing threshold reaches level 656. This time period until the recipient's hearing threshold reaches level 656 is then use to predict/determine when the recipient should return to the clinic for a future appointment.

In one example, the time period until the recipient's hearing threshold reaches level 656 is multiplied by a variance factor to determine when the recipient should return to the clinic. For example, as shown in FIG. 6, the time period (T) is four (4) years, which is multiplied by a variance factor of 0.8, thereby indicating that the recipient should return to the clinic in 3.2 years. The variance factor can, for example, be set to encompass a 50th percentile of hearing threshold drops, $90^{th}$ percentile of hearing threshold drops, etc. The variance factor can also or alternatively be a fixed value (e.g., 5 dB drop).

FIG. 6 illustrates an example in which the predicted time period for when the recipient should return to the clinic for a future appointment is determined from an estimated hearing threshold change. In alternative embodiments, the predicted time period for when the recipient should return to the clinic for a future appointment can be determined directly from audiograms or other audiological data (e.g., a certain difference between a forecast audiogram and a current or other forecast audiogram).

Predicting the time period for when the recipient should return to the clinic, as described herein, may lower overall audiologist costs (due to less audiologist visits overall) and provide better recipient patient outcomes (higher powered devices are provided to patients with decreasing hearing losses). Moreover, shorter audiologist sessions as part of the 'work' is completed automatically and can result in better device selection for recipients (lower power devices are provided to recipients with stable hearing losses).

It is to be appreciated that the techniques presented herein are not mutually exclusive and that the prediction of an estimated time for a future clinical appointment for a recipient can be combined with prediction of a recommendation of a hearing device for a recipient. In certain such embodiments, the estimated timing for future clinical appointments, including appointment cadence (e.g., how often and when the recipient should return to the clinic) can be used as a factor in determining which device is best for a recipient (e.g., use both clinical appointment cadence and predicted future hearing outcomes to select suitable devices for a recipient).

Figure 7:
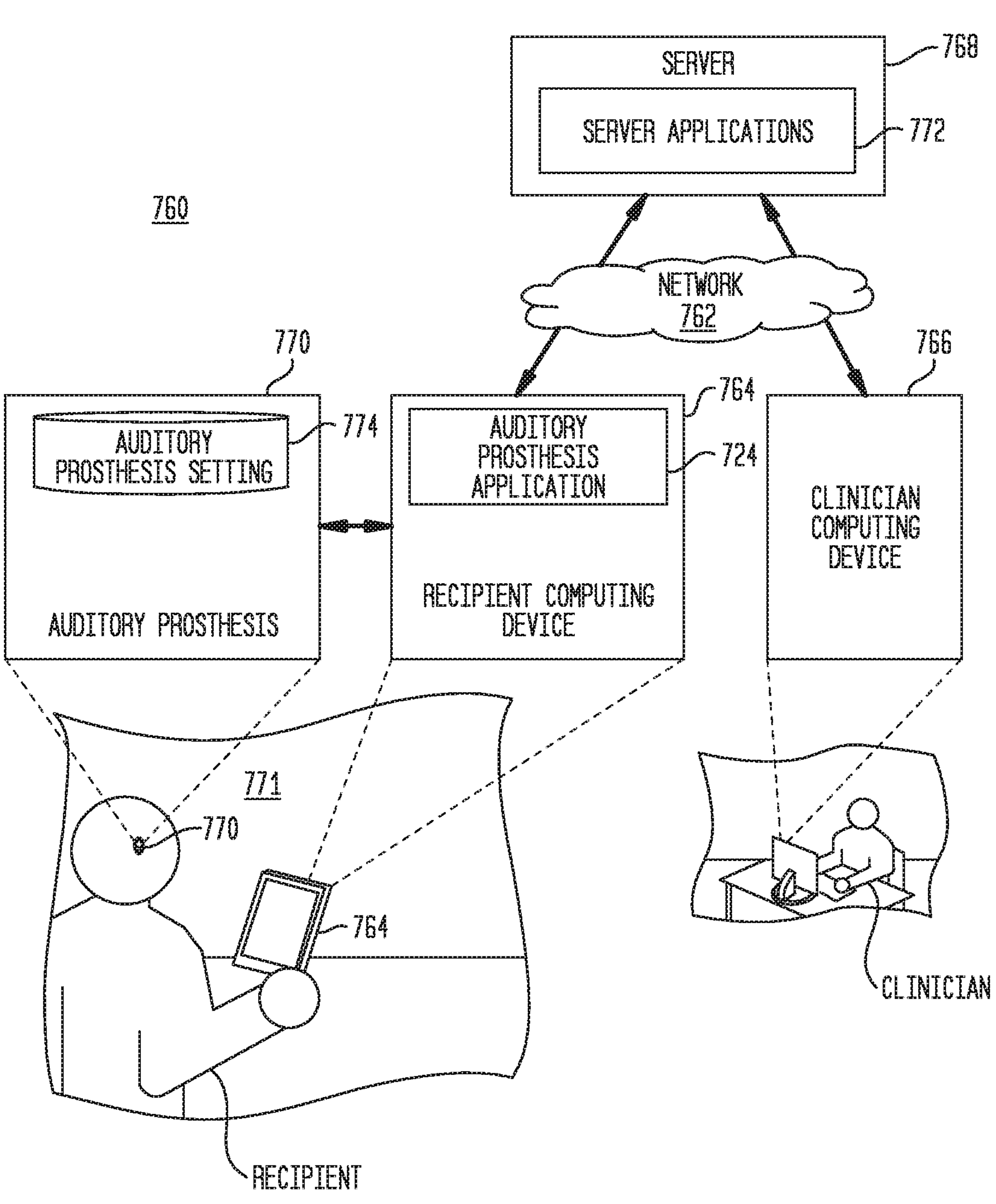
FIG. 7 is a schematic diagram illustrating an example auditory prosthesis system, with which aspects of the techniques presented herein may be implemented.

FIG. 7 illustrates an example auditory prosthesis system 760 that includes an auditory prosthesis 770 that can benefit from the use of technologies described herein. The system 760 further includes a recipient computing device 764, a clinician computing device 766, and a server 768, which are connected over a network 762. The network 762 is a computer network, such as the Internet, that facilitates the communication of data among computing devices connected to the computer network.

As illustrated, the auditory prosthesis 770 and the recipient computing device 764 are operated by the recipient in an environment 771. The auditory prosthesis 770 is a medical device relating to a recipient's auditory system, such as a cochlear implant or bone conduction devices (e.g., percutaneous bone conduction devices, transcutaneous bone conduction devices, active bone conduction devices, and passive bone conduction devices), and middle ear stimulators, among others. The auditory prosthesis 770 can take any of a variety of forms and operates according to auditory prosthesis settings 774.

The auditory prosthesis settings 774 are one or more parameters having values that affect how the auditory prosthesis 770 operates. For instance, the auditory prosthesis settings 774 can include a map having minimum and maximum stimulation levels for frequency bands of stimulation channels. The map is then used by the auditory prosthesis 770 to control an amount of stimulation to be provided. For instance, where the auditory prosthesis 770 is a cochlear implant, the map affects which electrodes of the cochlear implant to stimulate and in what amount based on a received sound input. In some examples, the auditory prosthesis settings 774 include two or more predefined groupings of settings selectable by the recipient. One of the two or more predefined groupings of settings may be a default setting.

The auditory prosthesis settings 774 can also include sound processing settings that modify sound input before it is converted into a stimulation signal. Such settings can include, for example, particular audio equalizer settings can boost or cut the intensity of sound at various frequencies. In examples, the auditory prosthesis settings 774 can include a minimum threshold for which received sound input causes stimulation, a maximum threshold for preventing stimulation above a level which would cause discomfort, gain parameters, loudness parameters, and compression parameters. The auditory prosthesis settings 774 can include settings that affect a dynamic range of stimulation produced by the auditory prosthesis 770. As described above, many of the auditory prosthesis settings 774 affect the physical operation of the auditory prosthesis 770, such as how the auditory prosthesis 770 provides stimulation to the recipient in response to sound input received from the environment 771.

The recipient computing device 764 is a computing device associated with the recipient of the auditory prosthesis 770. In many examples, the recipient computing device 764 is a cell phone, tablet computer, smart watch, etc., but can take other forms. Although described primarily in the context of the recipient, the recipient computing device 764 can be a computing device owned or primarily used by a parent or caregiver for the recipient.

In examples, the recipient computing device 764 includes an auditory prosthesis application 724 that operates on the recipient computing device 764 and cooperates with the auditory prosthesis 770. The auditory prosthesis application 724 is a computer program stored as computer-executable instructions in memory on the recipient computing device 764 that, when executed, performs one or more tasks relating to the auditory prosthesis 770. For instance, the auditory prosthesis application 724 can control the auditory prosthesis 770 (e.g., based on input received from the recipient), monitor usage of the auditory prosthesis 770, and obtain data from the auditory prosthesis 770. The recipient computing device 764 can connect to the auditory prosthesis 770 using, for example, a wireless radiofrequency communication protocol (e.g., BLUETOOTH). The auditory prosthesis application 724 transmits or receives data from the auditory prosthesis 770 over such a connection. The auditory prosthesis application 724 can also stream audio to the auditory prosthesis 770, such as from a microphone or an application running on the recipient computing device 764 (e.g., a video or audio application). In examples, the auditory prosthesis application 724 functions by obtaining data regarding the auditory prosthesis 770. The recipient computing device 764 can be in communication with one or both of the clinician computing device 766 and the server 768, such as via the auditory prosthesis application 724 communicating over the network 762.

The clinician computing device 766 is a computing device used by a clinician. A clinician is a medical professional, such as an audiologist. In an example, the clinician is a medical professional that provides care or supervision for the recipient. The clinician computing device 766 includes one or more software programs usable to monitor or control the auditory prosthesis 770, such as customization of the auditory prosthesis settings 774.

The server 768 is a server remote from the auditory prosthesis 770, recipient computing device 764, and the clinician computing device 766. The server 768 is communicatively coupled to the recipient computing device 764 and the clinician computing device 766 via the network 762. In many examples, the server 768 is indirectly communicatively coupled to the auditory prosthesis 770 through the recipient computing device 764 (e.g., via the auditory prosthesis application 724). In some examples, the server 768 is directly communicatively coupled to the auditory prosthesis 770. The server 768 includes one or more server applications 772. The one or more server applications 772 are computer programs stored as computer-executable instructions in memory on the server 768 that, when executed, perform one or more tasks relating to the system 760.

In general, the components of the system 760 can cooperate to perform aspects of the predictive consultation techniques presented herein. For example, in accordance with certain embodiments presented herein, the one or more server applications 772 are operable to, for example, perform one or more operations described herein, such as operations associated with data module 102 and predictive consultation module 104 of FIG. 1. However, the operations of associated with data module 102 and predictive consultation module 104 of FIG. 1 could also be partially or fully implemented by one or more of the recipient computing device 764 and/or the clinician computing device 766. The operations associated with output module 106 may be performed, for example, at the recipient computing device 764 and/or the clinician computing device 766.

As noted above, merely for ease of description, the predictive medical device consultation techniques presented herein are primarily described with reference to sensory devices and, more specifically, hearing devices. However, it is to be appreciated that the techniques presented herein may also be implemented in associated with other types of medical devices. For example, the techniques presented herein may be implemented with a variety of hearing devices, such as hearing aids, middle ear auditory prostheses, bone conduction devices, direct acoustic stimulators, electro-acoustic prostheses, auditory brain stimulators, etc. The techniques presented herein may also be used with other types of medical devices, including other types of sensory devices, such as vestibular devices (e.g., vestibular implants), visual devices (e.g., bionic eyes), etc., tinnitus therapy devices, sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 8:
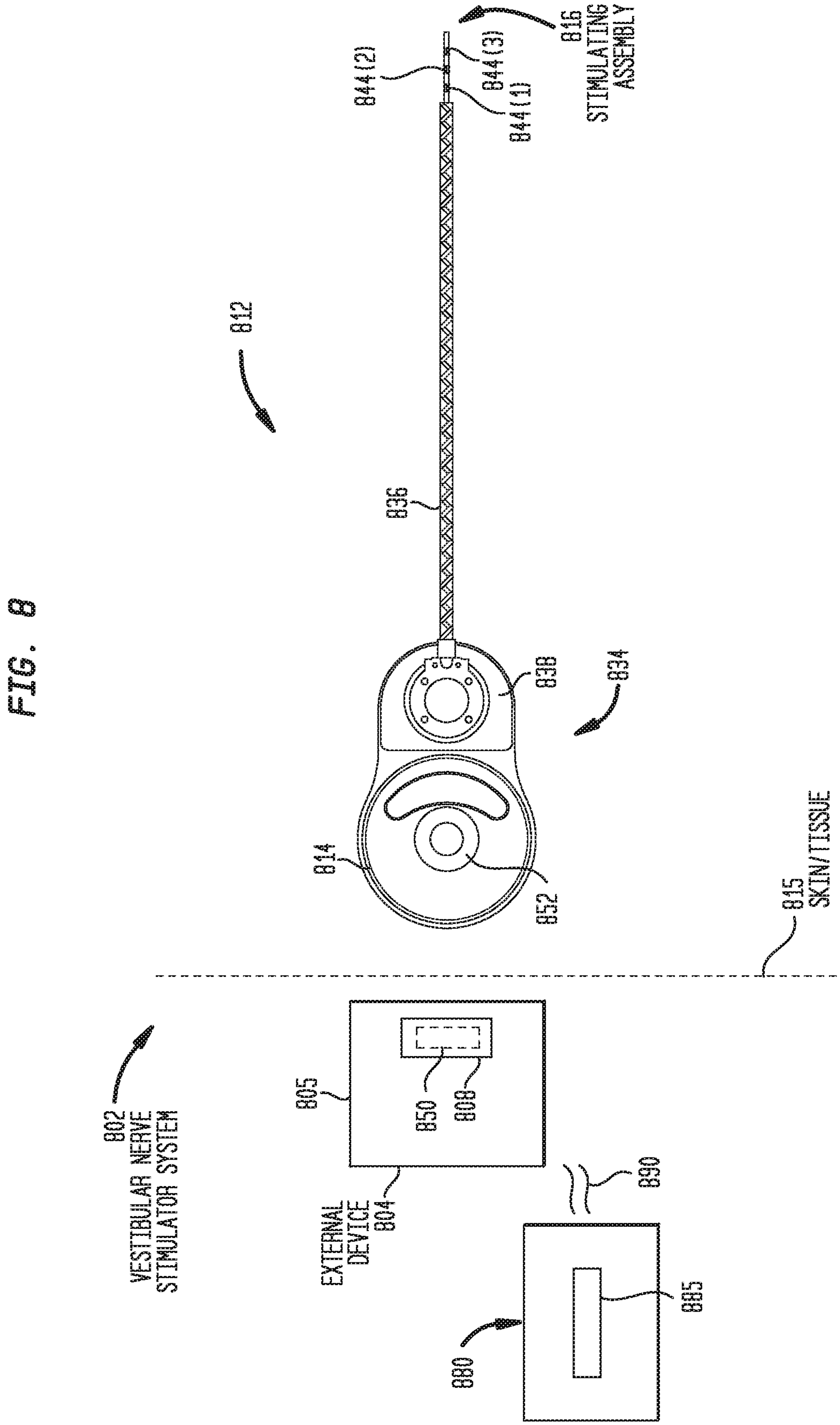
FIG. 8 is a schematic diagram illustrating an example vestibular stimulator system, with which aspects of the techniques presented herein may be implemented.

FIG. 8 illustrates an example vestibular stimulator system 802 with which aspects of the techniques presented herein may be implemented. In this example, the vestibular stimulator system 802 comprises an implantable component (vestibular stimulator) 812 and an external device/component 804 (e.g., external processing device, battery charger, remote control, etc.).

The vestibular stimulator 812 comprises an implant body (main module) 834, a lead region 836, and a stimulating assembly 816, all configured to be implanted under a skin/tissue flap (skin flap) 815 of the recipient. The implant body 834 generally comprises a hermetically-sealed housing 838 in which RF interface circuitry, one or more rechargeable batteries, one or more processors, and a stimulator unit are disposed. The implant body 834 also includes an internal/implantable coil 814 that is generally external to the housing 838, but which is connected to the transceiver via a hermetic feedthrough (not shown).

The stimulating assembly 816 comprises a plurality of electrodes 844 disposed in a carrier member (e.g., a flexible silicone body). In this specific example, the stimulating assembly 816 comprises three (3) stimulation electrodes, referred to as stimulation electrodes 844(1), 844(2), and 844(3). The stimulation electrodes 844(1), 844(2), and 844(3) function as an electrical interface for delivery of electrical stimulation signals to the recipient's vestibular system.

The stimulating assembly 816 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

In accordance with embodiments presented herein, the external device 804 can include an integrated external magnet 850 configured to be magnetically coupled to an implantable magnet 852 in the vestibular stimulator 812. The external device 804 also includes an integrated external coil 808 that is configured to be wirelessly (e.g., inductively) coupled to the implantable coil 814 of the vestibular stimulator 812. In FIG. 8, the external magnet 850 is shown using dashed lines, indicating the external coil 808 disposed around the magnet 850. The magnets 850 and 852 magnetically couple the external device 804 to the vestibular stimulator 812 through the skin flap 815.

Also shown in FIG. 8 is a computing device 880, which may be configured to implement aspects of the predictive consultation techniques and set operational parameters of the vestibular stimulator 812 based on the thereon. For example, the computing device 880 can include a memory and processor with logic 885. The computing device 880 can provide and/or display the predictions, etc. described above (e.g., to the recipient and/or a clinician aiding the recipient) and/or adjust one or more settings associated with the vestibular implant 802 based on the predictions via one or more data links 890, such as a wired connection, a wireless network, radio frequency, infrared, or another suitable wired or wireless communication mechanism or combinations thereof.

Figure 9:
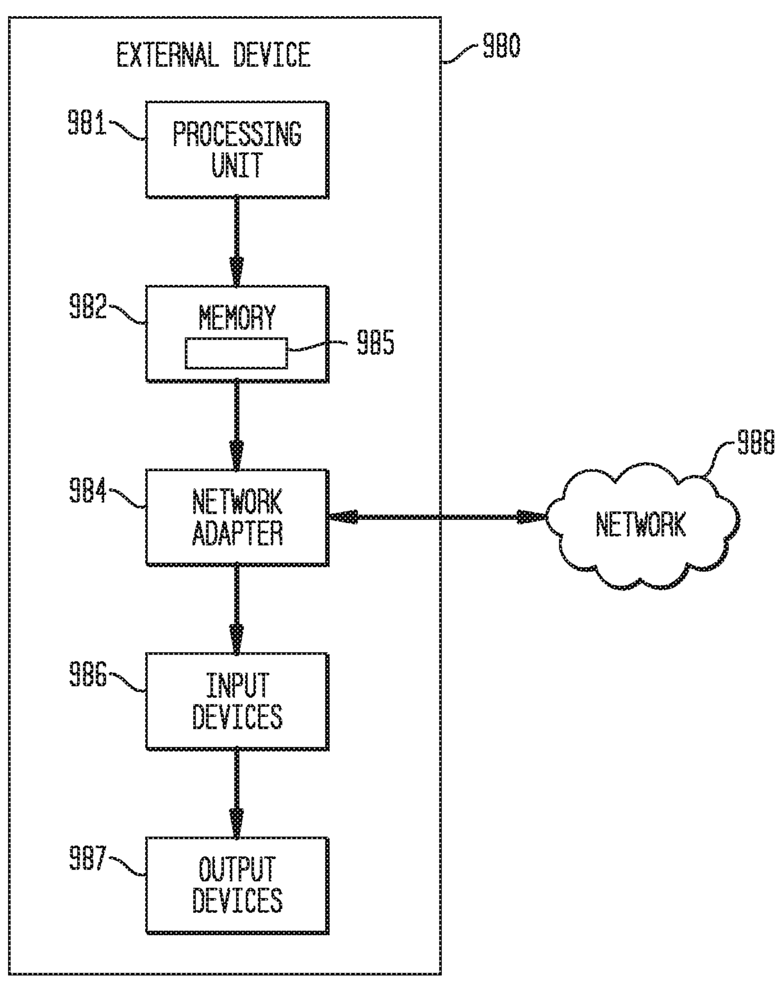
FIG. 9 is functional block diagram of a computing device configured to implement aspects of the techniques presented herein.

As noted above, aspects of the techniques presented herein can be implemented at a computing device in wired or wireless communication with a medical device. FIG. 9 illustrates an example of a suitable computing device 980 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing device 980 can be a single virtual or physical device operating in a networked environment over communication links to one or more remote devices. The remote device can be a hearing device, a personal computer, a server, a router, a network personal computer, a peer device or other common network node.

In its most basic configuration, computing device 980 includes at least one processing unit 981 and memory 982. The processing unit 981 includes one or more hardware or software processors (e.g., Central Processing Units) that can obtain and execute instructions. The processing unit 981 can communicate with and control the performance of other components of the computing device 980.

The memory 982 is one or more software or hardware-based computer-readable storage media operable to store information accessible by the processing unit 981. The memory 982 can store, among other things, instructions executable by the processing unit 981 to implement applications or cause performance of operations described herein, as well as other data. The memory 982 can be volatile memory (e.g., RAM), non-volatile memory (e.g., ROM), or combinations thereof. The memory 982 can include transitory memory or non-transitory memory. The memory 982 can also include one or more removable or non-removable storage devices. In examples, the memory 982 can include RAM, ROM, EEPROM (Electronically-Erasable Programmable Read-Only Memory), flash memory, optical disc storage, magnetic storage, solid state storage, or any other memory media usable to store information for later access. In examples, the memory 982 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 982 can include wired media such as a wired network or direct-wired connection, and wireless media such as acoustic, RF, infrared and other wireless media or combinations thereof. In certain embodiments, the memory 982 comprises predictive consultation logic 985 that, when executed, enables the processing unit 981 to perform aspects of the techniques presented.

In the illustrated example, the computing device 980 further includes a network adapter 984, one or more input devices 986, and one or more output devices 987. The system computing device 980 can include other components, such as a system bus, component interfaces, a graphics system, a power source (e.g., a battery), among other components.

The network adapter 984 is a component of the computing device 980 that provides network access (e.g., access to at least one network 988). The network adapter 984 can provide wired or wireless network access and can support one or more of a variety of communication technologies and protocols, such as ETHERNET, cellular, BLUETOOTH, near-field communication, and RF (Radiofrequency), among others. The network adapter 984 can include one or more antennas and associated components configured for wireless communication according to one or more wireless communication technologies and protocols.

The one or more input devices 986 are devices over which the computing device 980 receives input from a user. The one or more input devices 986 can include physically-actuatable user-interface elements (e.g., buttons, switches, or dials), touch screens, keyboards, mice, pens, and voice input devices, among others input devices.

The one or more output devices 987 are devices by which the computing device 980 is able to provide output to a user. The output devices 987 can include, displays (e.g., touch-screens), speakers, and printers, among other output devices.

Figure 10:
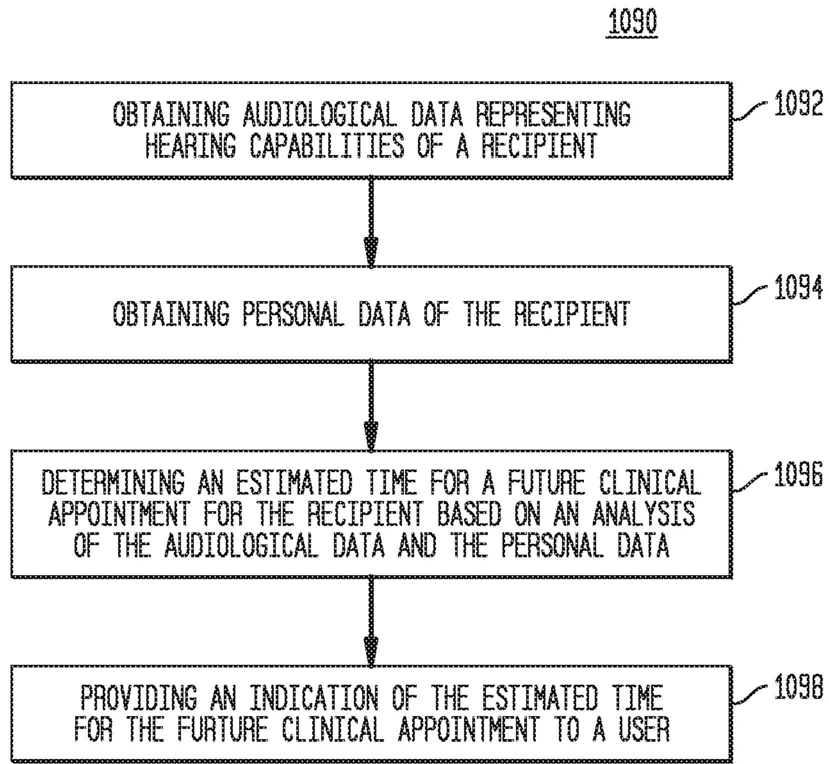
FIG. 10 is a flowchart of a method, in accordance with certain embodiments presented herein.

FIG. 10 is a flowchart of a method 1090, in accordance with embodiments presented herein. The method 1090, which is implemented at a computing device, begins at 1092 where the computing device obtains audiological data representing hearing capabilities of a recipient. At 1094, the computing device obtains personal data of the recipient. At 1096, the computing device determines an estimated time for a future clinical appointment for the recipient based on an analysis of the audiological data and the personal data. At 1098, the computing device provides an indication of the estimated time for the future clinical appointment to a user.

Figure 11:
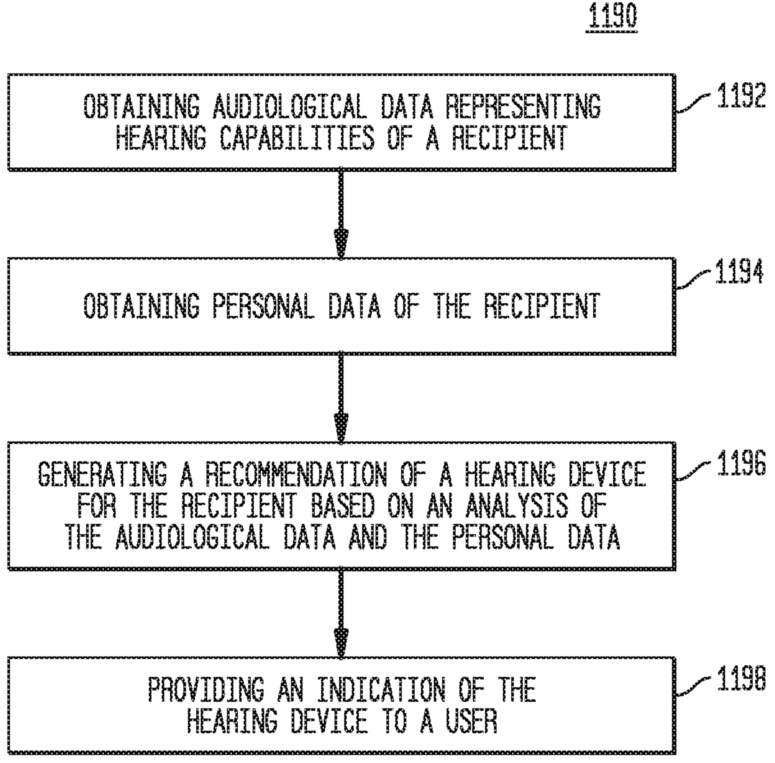
FIG. 11 is a flowchart of another method, in accordance with certain embodiments presented herein.

FIG. 11 is a flowchart of a method 1190, in accordance with embodiments presented herein. The method 1190, which is implemented at a computing device, begins at 1192 where the computing device obtains audiological data representing hearing capabilities of a recipient. At 1194, the computing device obtains personal data of the recipient. At 1196, the computing device generates a recommendation of a hearing device for the recipient based on an analysis of the audiological data and the personal data. At 1198, the computing device determines an estimated time for a future clinical appointment for the recipient based on an analysis of the audiological data and the personal data. At 1098, the computing device provides an indication of the estimated time for the future clinical appointment to a user.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:

at a computing device:

obtaining audiological data representing hearing capabilities of a recipient;

obtaining personal data of the recipient;

obtaining ancillary data related to a hearing device;

predicting, using an artificial intelligence system, one or more future hearing outcomes for the recipient based on an analysis of the audiological data, the personal data, and the ancillary data;

and instantiating, based on the one or more future hearing outcomes, one or more settings of the hearing device to change one or more operations of the hearing device.

2. The method of claim 1, wherein the artificial intelligence system is trained based on correlated normative data comprising personal data and audiological data associated with other hearing device recipients.

3. The method of claim 1, further comprising:

analyzing, using the artificial intelligence system, one or more audiograms representing the one or more future hearing outcomes to determine an estimated time period for the hearing capabilities of the recipient to undergo a predetermined change; and generating an estimated time for a future clinical appointment based on the estimated time period for the hearing capabilities of the recipient to undergo the predetermined change.

4. The method of claim 3, wherein determining, based on the one or more audiograms representing the one or more future hearing outcomes, an estimated time period for the hearing capabilities of the recipient to undergo a predetermined change comprises:

determining a current hearing level of the recipient; and estimating, based on the one or more future hearing outcomes, a time period for the current hearing level of the recipient to reach a second hearing level.

5. The method of claim 4, wherein the second hearing level is a level determined relative to the current hearing level of the recipient.

6. The method of claim 3, wherein generating the estimated time for the future clinical appointment based on the estimated time period for the hearing capabilities of the recipient to undergo the predetermined change comprises:

multiplying the estimated time period for the hearing capabilities of the recipient to undergo the predetermined change by a variance factor.

7. The method of claim 1, further comprising:

obtaining one or more clinical standards associated with a change in hearing loss requiring further clinical intervention; and generating an estimated time for a future clinical appointment based on the one or more future hearing outcomes and the one or more clinical standards.

8. The method of claim 1, wherein the recipient is a hearing device recipient using a hearing device for hearing rehabilitation, and wherein the method further comprises:

obtaining operational parameters associated with the hearing device; and generating an estimated time for a future clinical appointment for the recipient based on an analysis of the audiological data, the personal data, and the operational parameters associated with the hearing device.

9. The method of claim 1, wherein the one or more future hearing outcomes include a first evolution of hearing capabilities of the recipient over a future period with an aid of the hearing device and a second evolution of hearing capabilities of the recipient over the future period without the aid of the hearing device, and wherein the ancillary data comprises one or more device attributes of the hearing device, one or more costs associated with the hearing device, or a clinical time associated with use of the hearing device.

10. The method of claim 1, further comprising:

controlling, based on the instantiating, an amount of stimulation provided by the hearing device to the recipient.

11. A method, comprising:

at a computing device:

obtaining audiological data representing hearing capabilities of a recipient;

obtaining personal data of the recipient;

obtaining ancillary data related to a hearing device;

predicting, using an artificial intelligence system, one or more future hearing outcomes for the recipient based on an analysis of the audiological data, the personal data, and the ancillary data; and providing, based on the one or more future hearing outcomes, a treatment to the recipient, wherein the treatment includes a prescription of the hearing device.

12. The method of claim 11, wherein providing, based on the one or more future hearing outcomes, the treatment to the recipient includes:

generating a recommendation of the hearing device through a relative analysis of the one or more future hearing outcomes.

13. The method of claim 12, wherein predicting the one or more future hearing outcomes for the recipient based on the analysis of the audiological data and the personal data comprises:

generating one or more forecast audiograms for the recipient; and analyzing, using an artificial intelligence system, the one or more forecast audiograms to determine an estimated time period for the hearing capabilities of the recipient to undergo a predetermined change.

14. The method of claim 12, wherein predicting the one or more future hearing outcomes for the recipient based on the analysis of the audiological data and the personal data comprises:

predicting a plurality of future hearing outcomes for the recipient, wherein two or more of the plurality of future hearing outcomes are associated with predicted use of different hearing devices by the recipient.

15. The method of claim 12, wherein predicting the one or more future hearing outcomes for the recipient based on the analysis of the audiological data and the personal data comprises:

predicting a plurality of future hearing outcomes for the recipient, wherein two or more of the plurality of future hearing outcomes are associated with predicted use of at least one of one or more different hearing devices or different hearing device settings.

16. The method of claim 12, wherein predicting the one or more future hearing outcomes for the recipient based on the analysis of the audiological data the personal data comprises:

predicting a plurality of future hearing outcomes for the recipient, wherein one or more of the plurality of future hearing outcomes are associated with use of one or more hearing devices by the recipient, and at least one of the plurality of future hearing outcomes is associated with unaided hearing of the recipient.

17. The method of claim 11, wherein the hearing device comprises a cochlear implant, a hearing aid, or a bone conduction device, and wherein predicting, using the artificial intelligence system, the one or more future hearing outcomes for the recipient based on the analysis of the audiological data, the personal data, and the ancillary data comprises:

analyzing the audiological data, the personal data, and the ancillary data with the artificial intelligence system.

18. The method of claim 11, wherein providing, based on the one or more future hearing outcomes, the treatment to the recipient comprises:

generating a recommendation of the hearing device based on one or more hearing device attributes, wherein the one or more hearing device attributes include at least one of device size, device aesthetics, device battery use information, and device wearing method.

19. The method of claim 11, wherein providing, based on the one or more future hearing outcomes, the treatment to the recipient comprises:

generating a recommendation of the hearing device based on costs associated with one or more hearing devices.

20. The method of claim 11, wherein the recipient is a hearing device recipient using a hearing device for hearing rehabilitation, and wherein the method further comprises:

obtaining operational parameters associated with the hearing device; and generating a recommendation of a hearing device for the recipient based on an analysis of the audiological data, the personal data, and the operational parameters associated with the hearing device.

* * * * *